US008691347B2

(12) United States Patent
Varfolomeev et al.

(10) Patent No.: US 8,691,347 B2
(45) Date of Patent: Apr. 8, 2014

(54) METHOD FOR PRODUCING POLYMER COATING ON PARTICLE SURFACES

(75) Inventors: Sergey Dmitrievich Varfolomeev, Moscow (RU); Vladimir Mikhailovich Goldberg, Moscow (RU); Alexander Nikitovich Shchegolikhin, Moscow (RU); Anatoly Alexandrovich Kuznetsov, Moscow (RU)

(73) Assignee: Emanuel Institute of Biochemical Physics of Russian Academy of Sciences (IBCP RAS), Moscow (RU)

( * ) Notice: Subject to any disclaimer, the term of this patent is extended or adjusted under 35 U.S.C. 154(b) by 842 days.

(21) Appl. No.: 12/743,370

(22) PCT Filed: Nov. 11, 2008

(86) PCT No.: PCT/RU2008/000703
§ 371 (c)(1),
(2), (4) Date: May 18, 2010

(87) PCT Pub. No.: WO2009/067046
PCT Pub. Date: May 28, 2009

(65) Prior Publication Data
US 2010/0260942 A1    Oct. 14, 2010

(30) Foreign Application Priority Data
Nov. 21, 2007    (RU) ................................ 2007142696

(51) Int. Cl.
*C08F 2/46*    (2006.01)
(52) U.S. Cl.
USPC ............................ 427/521; 427/508; 427/520
(58) Field of Classification Search
USPC .......................................... 427/508, 520, 521
See application file for complete search history.

(56) References Cited

U.S. PATENT DOCUMENTS 5,292,864 A * 3/1994 Wood et al. .................... 528/490
6,274,387 B1 * 8/2001 Yamauchi et al. ............. 436/526
(Continued)

FOREIGN PATENT DOCUMENTS

JP    63005019 A    1/1988
JP    8176461 A     7/1996
(Continued)

OTHER PUBLICATIONS

Khimicheskaya Entsiklopediya, Moscow, Bolshaya Rossiskaya Entsiklopedia, 1992, vol. 3, p. 423-424, col. 838, lines 17-21, col. 839, lines 1-3.

(Continued)

*Primary Examiner* — Elena T Lightfoot
(74) *Attorney, Agent, or Firm* — Ladas & Parry LLP

(57) ABSTRACT

The invention concerns the methods for producing polymeric coatings on particle surfaces and can be used in pharmacology, medicine, veterinary and cosmetology to create the systems of vector delivery of drugs and biologically active agents as well as in other fields applying the particles with thin-layer polymer coatings. The method enables to obtain biocompatible, particularly polyamide and polyimide coatings on inorganic particles including magnetic inorganic nanoparticles. The method for producing polymeric coatings on particles surface comprises (a) forming a reaction system containing the particles mixed with monomers, and (b) the subsequent carrying out of polymerization reaction to form the polymeric coating on the particles; wherein the said polymerization reaction is accomplished by irradiating the reaction system with electromagnetic radiation, particularly, with microwaves capable of being absorbed partially or totally by the said particles.

3 Claims, 6 Drawing Sheets

(56) References Cited

U.S. PATENT DOCUMENTS

| | | |
|---|---|---|
| 6,586,097 B1 * | 7/2003 | Pascault et al. ............... 428/402 |
| 2005/0112154 A1 * | 5/2005 | Giroud et al. ................. 424/401 |
| 2007/0172426 A1 | 7/2007 | Lee et al. |
| 2008/0004364 A1 * | 1/2008 | Huo et al. .......................... 522/2 |

FOREIGN PATENT DOCUMENTS

| | | |
|---|---|---|
| WO | 9627627 A1 | 9/1996 |
| WO | 01/28771 A1 | 4/2001 |

OTHER PUBLICATIONS

English abstract of JP 63005019 A, Jan. 11, 1988.

English abstract of JP 8176461 A, Jul. 9, 1996.

* cited by examiner

US 8,691,347 B2

METHOD FOR PRODUCING POLYMER COATING ON PARTICLE SURFACES

FIELD OF THE INVENTION

The invention concerns nanotechnologies, nanomaterials, bioengineering technologies, technologies for creation of biocompatible and bioactive materials as well as it is applicable for preparing new thin-film functional and semi-functional polymeric coatings on particles, applicable for creation of vector delivery of drugs and biologically active agents in practical medicine and veterinary, medicinal and pharmacological industries, biotechnology, agriculture, industries for cosmetic and hygienic products, as well as in separation technologies. The claimed method is applicable in developments of promising technologies for creation of new nanomaterials and high-dispersion systems with specific properties.

Polymeric coatings are widely applied in various technical fields: the data recording, storage and display, the electronic and optoelectronic instruments and devices, the separation technologies, the magnetic fluids production, the industries for equipment and accessories for medicine, pharmacology, biotechnology, bioengineering, cosmetology, chemical and food industries; for functionalization, modification and protection of all surfaces—including those of inorganic particles—in biomedical pharmaceutical, sensor, analytical and diagnostic technologies, etc.

DESCRIPTION OF THE RELATED ART

Broad potentials of practical applications of such materials cause the presence of a wealth of patents describing the methods for preparing the polymer coatings on particle surfaces. The documents listed below do not encompass all variety of known methods. They, however, characterize the most commonly applied approaches coming to the procedures for coating the particle surfaces with some ready-made polymer materials or to forming the coatings with some predetermined properties via polymerization of monomers on particle surfaces under the action of initiating factors.

U.S. Pat. Appl. No. 20070172426 describes the method for preparing the polymeric coating on microparticles. It comprises: (a) preparing the size-homogenous particles (1-100 nm in diameter); (b) hydrophobization of nanoparticle surfaces; (c) preparing suspension of hydrophobic particles and of polymerization initiator in a hydrophobic solvent; (d) emulsification via dispersion of the hydrophobic solvent drops in an aqueous phase and in an emulgent presence; (e) preparing an emulsion wherein the drop sizes vary within 2-20 nm; (f) partial evaporation of the hydrophobic drops to form microdrops in the aqueous phase; (g) replacement of the starting surfactant with a polymerizable surfactant; (h) addition of a polymerizable monomer into the aqueous phase and its adsorption onto the particles; (i) polymerizing the monomers to provide a polymer layer onto the microparticles; (j) subsequent functionalizing the polymeric particle surface by other polymers or by particles, or by biological macromolecules. The polymer layer on particle surfaces was formed in said method by UV irradiation or by heating up to 75° C., using a certain-type initiator. Major drawbacks of the method are multiple stages required and the necessity to use stabilizers and emulgators which can contaminate the resultant material.

U.S. Pat. Appl. 20030232196 describes the method for formation of a polymeric coating on particles using the thermal treatment of the coating material being a polymer selected out of a group of polyorganosiloxanes or their mixtures. The method is intended for preparing the materials applicable in constructions of electromagnetic devices. A possibility of its application for creation of biocompatible polymer coatings on particle surfaces has not been claimed in the patent.

JP Pat. Appl. No. 2005160378 describes the method for preparing the polymeric coating onto magnetic particles. The said method comprises the formation of a polymer layer on particles, using the cross-linking; the polymer has the functional groups interacting with physiologically active agents.

JP Pat. Appl. No. 2006088131 describes the method to prepare a uniform and stable polymeric coating on magnetic particles. The said method comprises (a) absorption of a hydrophobic material on hydrophilic particles; (b) hydrophylization of surfaces of hydrophobized particles via ionic strength decrease by surfactants having nonionic hydrophilic groups; (c) obtaining the resultant dispersed fluid. The said method also comprises (d) emulsifying a monomer solution using ionic and nonionic surfactants; (e) combining the emulsion and the dispersed fluid; (f) emulsion polymerization of a liquid emulsion. As a result, the magnetic particles coated with the polymer layer are formed. A drawback of the method is its complexity, many steps, a necessity to use solvents and additional surfactants.

JP Pat. No. 7082302, describes the method to prepare a composite nanostructure in the form of polymer cores, coated with ferrite particles with a protective polymer coating formed on their surfaces. The method comprises (a) coating the polymer core with ultra-fine ferrite particles and subsequent coating with a protective polymer layer formed by radical polymerization of unsaturated monomers which can contain glycidyl groups; (b) employment of polymerization initiator, which requires an additional purification of the resultant product.

JP Pat. No. 63005019, describes the method to prepare a polymeric coating on magnetic particles. It comprises the encapsulation of magnetic particles and creation, on their surfaces, of polymeric coating containing immobilized biological components (proteins, enzymes). The said method uses, as the core particles, ferromagnetic materials, such as Fe, Co, Ni and magnetite. The particles are coated with a linking molecular layer containing organic-silicon compounds. The polymer coating is formed via polymerization of functional groups on the particle surface and polymerizable monomers, in particular methyl acrylate. The polymer coating is formed in multiple steps, what hinders the process of preparing the encapsulated standard-composition particles.

WO Pat. No. 9102811 describes the method for preparing the polymeric coating on magnetic particle surfaces. It aims to preparing the coated bioactive magnetic particles usable for obtaining magnetic-resonance images. The method permits to prepare the polymer coating on particles with the aid of reducing the particle size of the initial crystalline material by sonication in presence of a coating agent. Thus coated magnetic particles form a stable colloidal system, but, expectedly, the obtained particles should have rather wide distribution in particle size and thickness of the coating.

U.S. Pat. No. 4,677,027 describes the method for preparing the polymeric coating on particles containing immobilized metallic ions. The method consists of the replacement of immobilized metallic ions on the particles surface by a hydrophilic polymer through chemosorption. Inorganic particles, for instance magnetite particles, were put in contact with a solution containing a polymer reagent interacting with chelate reagent adsorbed on the particle. Thus prepared polymer layer can be a layer of polyalcohol, polyamine, polysaccharide, protein or peptide, polyacrylamide etc. The polymeric coating on particles by the said method is formed in multiple steps and is quite laborious and time-consuming.

WO Pat. Appl. No. 2004042397 describes the method for preparing a polymer coating on magnetic particles. The said method comprises (a) adsorption of a hydrophobic monomer (oligomer), preferably polyvinylpyrrolidone, (molecular mass 500-100), having polymerizable vinyl groups; (b) addition of a monomer having a carboxyl group and being a hydrophilic vinyl compound; (c) addition of a cross-linking agent 2,2'-azobis(isobutyronitrile), initiating a radical co-polymerization. The drawback of the method is a possible presence of residual quantities of the initiator in the suspension of resultant particles.

KR Pat. Appl. No. 20040060236 describes the method for coating solid-state substrates, including silicon, gold and polymer nanoparticles, with a layer of biodegradable poly-1,4-dioxan-2-on. The method comprises (a) bringing a catalyst and 1,4-dioxan-2-on into contact with a solid substrate having surface hydroxyl groups; (b) catalytic polymerization on substrate surface at 55-100° C. Likewise, as in the previous case, the necessity to use the catalyst results in the necessity of an additional purification of the resultant product of undesirable admixtures.

JP Pat. Appl. No. 2006213592 describes the method for preparing the polymeric coating on semiconductive nanoparticles, permitting to obtain the material with a high chemiluminescent activity and a high chemical stability. The method comprises the electrostatic binding of the polymer with the nanoparticle surface and the subsequent cross-linking of the polymeric molecules, thus providing a higher stability of the coating.

CA Pat. No. 2424082 describes the method for preparing the polymer coating on surfaces of semiconductive metallic nanoparticles. The said method comprises the adsorption of amphiphilic polymeric molecules on surfaces of hydrophobic particles under heating or vacuum evaporation of the polymer solution in non-aqueous, mostly non-polar solvent. If a polymer contains ionizable groups, they are preconverted into salt residues by adding relevant acidic and alkaline agents. The resultant material features a high dispersancy in water and is capable of further functionalization. The method supposes the use of organic solvents, cross-linking agents and other components undesirable from the viewpoint of ecology and purity of the end product.

CN Pat. No. 1506399 describes the method for preparing magnetic particles of ferrum oxide, whose surface is coated with a polymeric coating. The method allows one to prepare a polypyrrole polymeric coating on the surface of ferrum oxide particles (core-shell structure) by dispersing ferrum oxide particles in the reaction system which includes a trivalent ferrum salt, deionized water, monomer and oxidizer in the reactor under agitation. Supposedly, the presence in the reaction system of many components can result in non-uniform composition and presence of undesirable admixtures in the resultant product.

As prototype of the claimed invention, we address to JP Pat. No. 8176461 that describes the method for preparing a polymer coating on magnetic particles, by forming a polymer coating on the surface of magnetic particles, such as iron oxides, iron-nickel and iron-cobalt alloys. The polymer coating is formed via copolymerization of monomers; acrylic acid and acrylamide are used as hydrophilic monomers; methyl methacrylate and styrene are used as hydrophobic monomers. The polymer coating is formed via polymerization of the monomers on particle surfaces in presence of polymerization initiator. The polymerization is accomplished in a water solution or dispersion for 2-24 h at 40-100° C. Thickness of the resultant polymer coating is about 0.01 μm.

Analysis of the known methods for preparing the polymer coatings on particles shows them to be usually multi-step processes supposing the use of initiators, catalysts, coupling agents, solvents, and other agents, which necessitates an additional labor and time to purify the end product and to utilize the waste.

DETAILED DESCRIPTION OF THE INVENTION

The aim of the present invention is to devise a new method for producing polymer coating on particles, in particular biocompatible coatings on the surface of magnetic particles.

The stated aim is achieved by the claimed method for producing a polymer coating on the particles surface.

The claimed method for producing polymer coating on the particles surface comprises (a) forming a reaction system containing the particles mixed with monomers, and (b) the subsequent carrying out of polymerization reaction to form the polymeric coating on the particles; wherein the said polymerization is accomplished by irradiating the reaction system with electromagnetic radiation capable of being absorbed by the said particles, the surfaces of which is subjected to a polymer coating formation.

As electromagnetic radiation, it is possible to use microwaves and radio waves. The energy of electromagnetic waves absorbed by the particles is transformed into heat which causes a local heating of the particles at the space in the vicinity of every particle. The local rise of temperature in these space regions is responsible for conveying thermally-induced polymerization reactions right in the locus closely adjacent to the particles surface.

As the particles, the surfaces of which is subjected to a polymer coating formation, inorganic particles absorbing the electromagnetic radiation chosen from the corresponding regions of the electromagnetic spectrum can be used. As the said particles, magnetic particles which are known to be able to absorb the electromagnetic radiation of microwave and radio ranges can be used.

The claimed method permits to form a biocompatible polymer coating on the said particles. As the said monomers capable of forming the polymer coating, amino acids can be used. Aspartic acid can be used as the said amino acid.

The claimed method allows one to prepare biocompatible polyamide and polyimide or, in particular, polypeptide coatings on the said inorganic particles. Specifically, when aspartic acid is used as the monomer, the biocompatible coating of polysuccinimide (PSI) can be prepared which under a mild alkaline hydrolysis is converted into the salts of polyaspartic acid. It is obvious that the preparing of the PSI coating on the nanoparticles by other methods known in the art would require that it PSI be predissolved. However, when developing the present-day technologies, it is desirable to avoid employment of solvents since this usually entails ecological problems. Moreover, the most appropriate solvents for PSI dissolution, dimethyl formamide and dimethyl sulfoxide, are rendered to be quite toxic agents. The claimed method permits to obviate employment of toxic organic solvents.

An essential distinction of the claimed method from the methods known in the prior art consists in the fact that the polymerization of the monomers is performed under the action of electromagnetic radiation absorbed by the particles, and the polymer coating is formed on the surface of the said particles by virtue of a local heating of the reaction system only in the areas closely adjacent to the particles surfaces. Consequently, the claimed method requires employment of the particles which are able to absorb the electromagnetic radiation from the corresponding range of the electromagnetic spectrum or the particles which possess electronic conductivity.

The claimed method is suitable for preparing the said polymer coatings on surfaces of any particles capable of absorbing electromagnetic radiation from the said range. Any monomers which are able to undergo thermally-induced polymerization can be used as the said monomer. The method allows one to prepare various polymer coatings including the biocompatible ones and provides a possibility to control the coating layer thickness via selection of optimal power and time of irradiation.

The merits of the claimed method are: (a) a notable complexity and cost reduction of the technology for preparing the polymer coatings on particles, including the nanoparticles finding extensive use in various contemporary technologies, (b) a possibility to prepare biocompatible coatings, (c) ecological friendliness, (d) a relative simplicity. The method obviates the use chemical initiators, catalysts, coupling agents and toxic organic solvents which can become potential pollutants of the end product. As the reactor for realization of the claimed method, any vessel produced from radiation-inert material, for instance glass, can be used. As the radiation source, magnetron or any suitable industrial, laboratory, or domestic radiation generators, e.g., such as a microwave stove, can be used.

More specifically, as possible impurities or by-products in preparing the polymeric coating of PSI the unreacted aspartic acid and the minor quantities of unbound PSI can be present in the system; the unbound PSI being occasionally formed in the space between the particles remote from the particles surface upon irradiation of the reaction system bulk. The coated magnetic particles can be easily separated from the said possible admixtures, impurities and by-products by washing the reaction mixture with water and by magnetic separation.

A useful feature of the claimed invention is it provides the stable and coherent biocompatible polymer coating on the magnetic particles surface, thus notably expanding the possibilities of practical application of magnetic nanoparticles. The claimed invention provides simplified and more economic method for preparing the polymer coatings on magnetic nano-particles and facilitates development of ecologically pure mass productions of biocompatible polymer-coated magnetic nanomaterials applicable in medicine, medical diagnostics, pharmaceutical and other industries.

The technical result of the invention consists in the fact that it makes possible to prepare coherent polyamide and polyimide biocompatible coatings on the particles capable of absorbing electromagnetic waves. The claimed method permits one to prepare the polymer coatings on magnetic nanoparticles, applicable for further modification and functionalization, which makes possible to widely apply them in medical practice, veterinary, pharmacology, biotechnologies and other fields.

The claimed method opens up possibilities for development of ecologically pure technologies for production of magnetic nanomaterials coated with biocompatible polymers which are suitable for application in diagnostic, pharmacological and other industries.

EXAMPLE OF THE INVENTION EMBODIMENT

Figure 1:
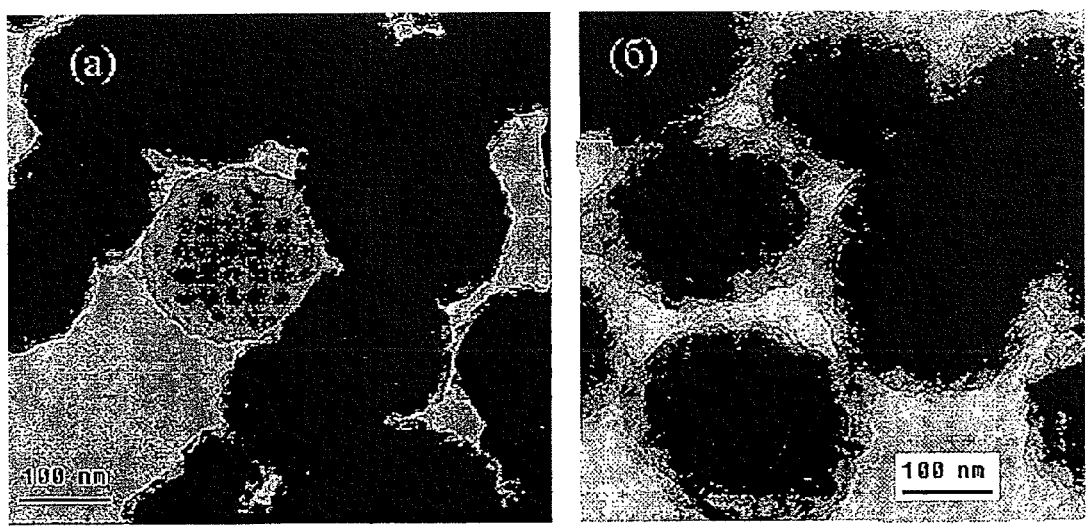
FIG. 1. Electronic microphotographs of nickel-copper alloy nanoparticles (12% copper) used in Example of the preferred embodiments of the invention: (a)—Pristine nanoparticles (before treatment); (b)—Nanoparticles treated as described in the Example of the preferred embodiments of the invention, isolated from the reaction mixture with the aid of hot water washing and magnetic separation.

Preparing the Polymeric Coating of Polysuccinimide (PSI) on Ferromagnetic Nickel-Copper Alloy Nanoparticles The PSI coating on the magnetic nickel-copper alloy nanoparticles was prepared by using L-aspartic acid ("Panreac" Spain) as the monomer having total impurities content less than 0.8%. The used pristine magnetic nickel-copper alloy (12% copper content) nanoparticles were of ~100 nm in size and have been obtained by dehydration and reduction of the corresponding hydroxides in hydrogen flow at an elevated temperature in the presence of Calcium ions. The said nanoparticles are used in hyperthermia (destruction via local heating in magnetic field) cure of cancer in mice. The electronic microphotograph of the said nanoparticles is shown in FIG. 1(*a*). The particles are seen to have spheric form and the medium size of ~100 nm.

The reaction system was prepared by thorough intermixing of 0.1 g of the magnetic nickel-copper alloy nanoparticles with 2.0 g of aspartic acid; the mixture was placed into a reactor (microwave stove) and electromagnetically irradiated (600 wt) for 15 min. Comparison of the electronic microphotographs in FIG. 1(a,b) shows that the size of the particles treated by the described process notably increased due to the polymeric coating formation on the nanoparticles surfaces.

Figure 2:
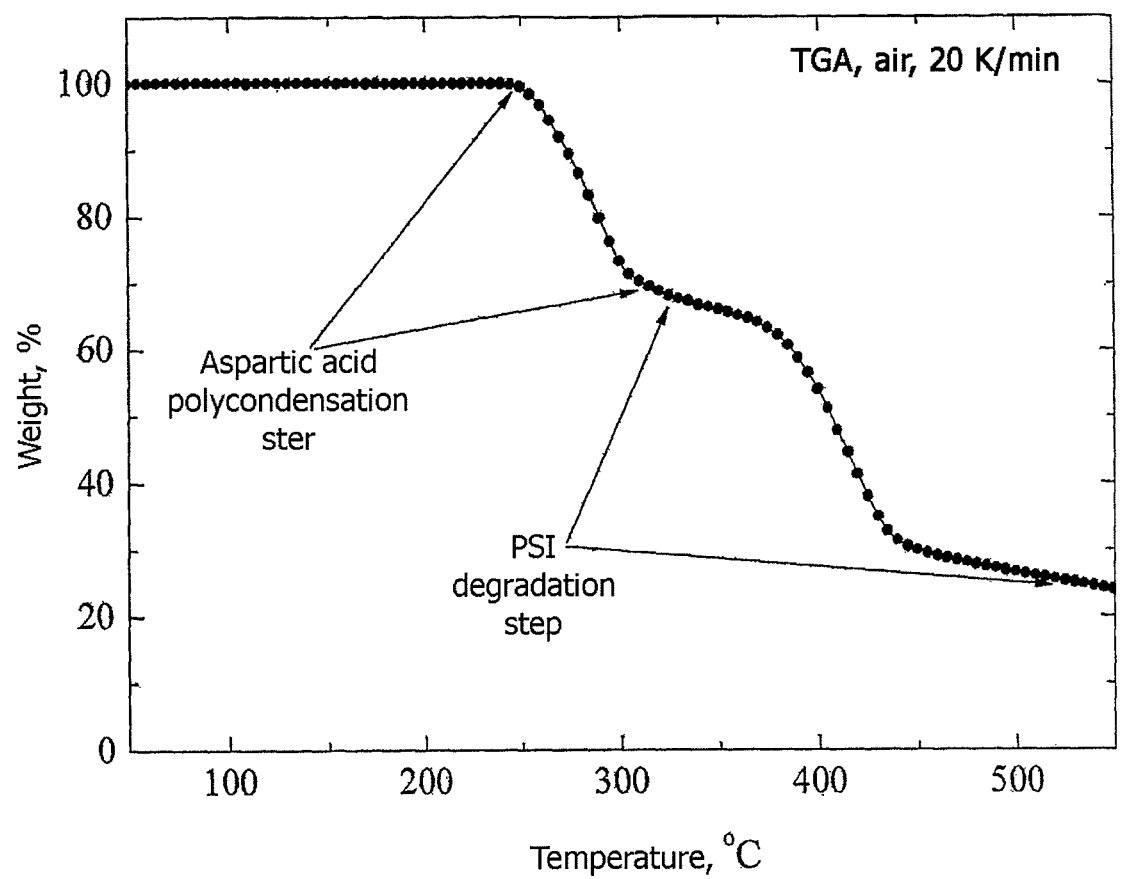
FIG. 2. Weight loss of aspartic acid sample in the course of dynamic thermogravimetric analysis (TGA) in air at the heating rate of 20 K/min: 1—aspartic acid polycondensation step; 2—PSI degradation step.

To clarify the nature of the processes of the polymeric coating formation in more detail, we had to reinvestigate beforehand the processes of transformation of aspartic (aminosuccinic) acid to PSI polymer by the conventional liquid-phase catalytic polymerization (polycondensation) route [Synthesis and characterization of biodegradable poly(L-aspartic acid-co-PEG)", Chee-Youb Won, Chih-Chang Chu, Jong Doo Lee, Journal of Polymer Science Part A: Polymer Chemistry, Vol. 36, Issue 16, pp. 2949-2959, 1998]. Water was shown to be the only volatile by-product in the investigated amino acid polycondensation reaction. Since the working temperature range of this process is around 200° C., the-released water should evaporate from the reaction mixture in the course of the reaction, and the overall process can be monitored with the aid of thermogravimetric analysis (TGA) wherein a sample weight loss is automatically measured with a high precision as a function of the process temperature. FIG. 2 shows that TGA curve permits to reliably identify the temperature ranges at which, first, PSI is formed from aspartic acid (200-250° C.) and, then, PSI is thermally degraded (350-800° C.).

Figure 3:
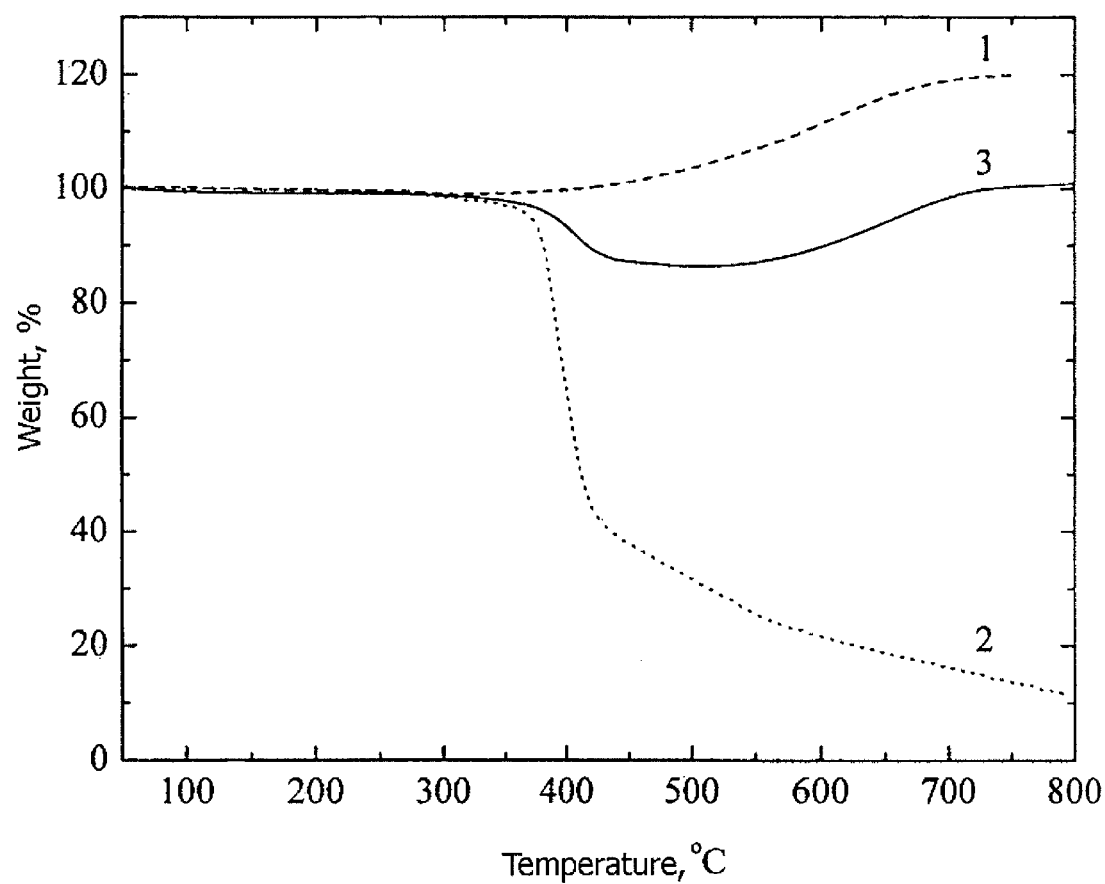
FIG. 3. Weight changes of the samples in the course of dynamic TGA in air at the heating rate of 20 K/min.: 1—Pristine nickel—copper alloy nanoparticles used in example 1 of the claimed method; 2—A sample of the standard PSI prepared by the liquid phase catalytic polymerization; 3—Nickel-copper alloy nanoparticles, treated as described in the Example of the preferred embodiments of the invention, isolated from the reaction mixture with the aid of hot water washing and magnetic separation.

FIG. 3 compares the TGA curves acquired in the result of dynamic heating of the samples in air at the rate of 20 K/min: 1—Pristine nickel-copper alloy nanoparticles used in the claimed method embodiment example; 2—Standard PSI prepared by the conventional liquid phase catalytic polymerization; 3—Nickel-copper alloy nanoparticles, treated as described in the invention embodiment example and isolated from the reaction mixture by hot water washing and magnetic separation. The TGA curves show that all samples practically retain their weight up to 300° C. Upon further heating, the pristine nanoparticles gain weight within the temperature range of 350-650° C. due to the accelerated oxidation of metals (curve 1). PSI, on the contrary, drastically loses weight within the range of 350-400° C. due to thermal-oxidative degradation (curve 2). Ad hoc conducted experiments showed that the first step (350-400° C.) represents carbonization of polysuccinimide, while the second step (400-800° C.) is due to oxidation and burning of the produced coke. Curve 3 is a superposition of curves 1 and 2. The observed fall in weight of the particles, produced by the claimed method and purified of all possible admixtures, can only be due to thermal-oxidative degradation of polysuccinimide, formed on the particle surfaces. So, curve 3 helps estimate a relative PSI quantity, formed on the particles, which was about 13 mass. %. The relative weight of the core of the nickel-copper alloy magnetic nanoparticles was about 87 mass. %. The weight increase in PSI—coated magnetic nanoparticles, observed in TGA experiments at 550-700° C., was due to oxidation of the metallic cores of the nanoparticles (formation of metallic polyoxides) after termination of the thermal-oxidative degradation of the organic coating.

Figure 4:
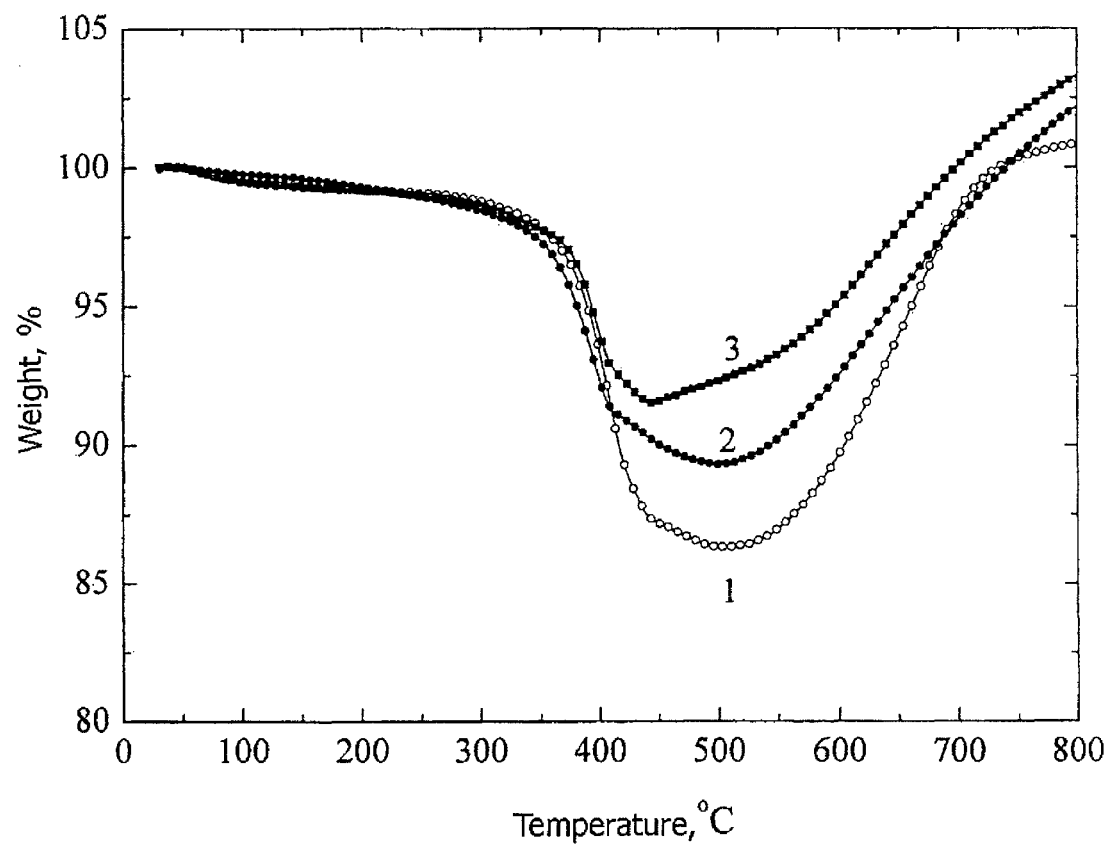
FIG. 4. Change in weight of the nickel-copper alloy nanoparticles covered with the polymer coatings formed by various procedures as measured in the course of dynamic TGA mode in air at the heating rate of 20 K/min/: 1—Nanoparticles treated as described in Example of the preferred embodiments of the invention and isolated from the reaction mixture with the aid of hot water washing and magnetic separation; 2—PSI-coated nanoparticles prepared by application of PSI from the solution thereof in the mixture of dimethyl formamide/methylene chloride (DMFA/MC) solvents; 3—Nanoparticles containing PSI coating which has been prepared by application of the coating from PSI/DMFA aerosol with subsequent hot air drying.

For comparison, the coating of the same nanoparticles with polysuccinimide was tried via sedimentation of PSI from solution thereof in methyl formamide/methylene chloride solvents mixture as well as by application of PSI from aerosol in dimethylformamide with subsequent hot air drying of the particles. The corresponding TGA results are shown in FIG. 4. The particles prepared by the three procedures contain the organic material which burnt out at temperatures above 300° C. and which based on its characteristic behavior at higher temperatures, was identified as polysuccinimide. The content of polysuccinimide formed on the nanoparticles surface, when applied with accordance with the preferred embodiment, turned out to be greater than in two other cases. Comparison of TGA curves in FIG. 4. shows that the nanoparticles, treated as described in the example of preferred embodiment of the invention and isolated from the reaction mixture with the aid of hot-water washing and magnetic separation (curve 1), hold about 13 mass % PSI fixed on their surface and, by this parameter, clearly surpass the other two samples of the nanoparticle which were coated with PSI by using toxic solvents (curves 2 and 3). Note that, due to the higher PSI content, the magnetic nanoparticles prepared in accordance with the preferred embodiments of the invention are superior also in terms of continuity and coherence of the polymeric coating as compared the control samples (curves 2 and 3).

The PSI coating prepared on the surface of the pristine nickel-copper alloy nanoparticles as described in the example of the preferred embodiments of the invention is quite firmly fixed on the nanoparticles surface, that is, is coherent: such coating withstands multiple magnetic separations and washings of the nanoparticles by hot water during intensive mechanical agitation of water suspensions.

Figure 5:
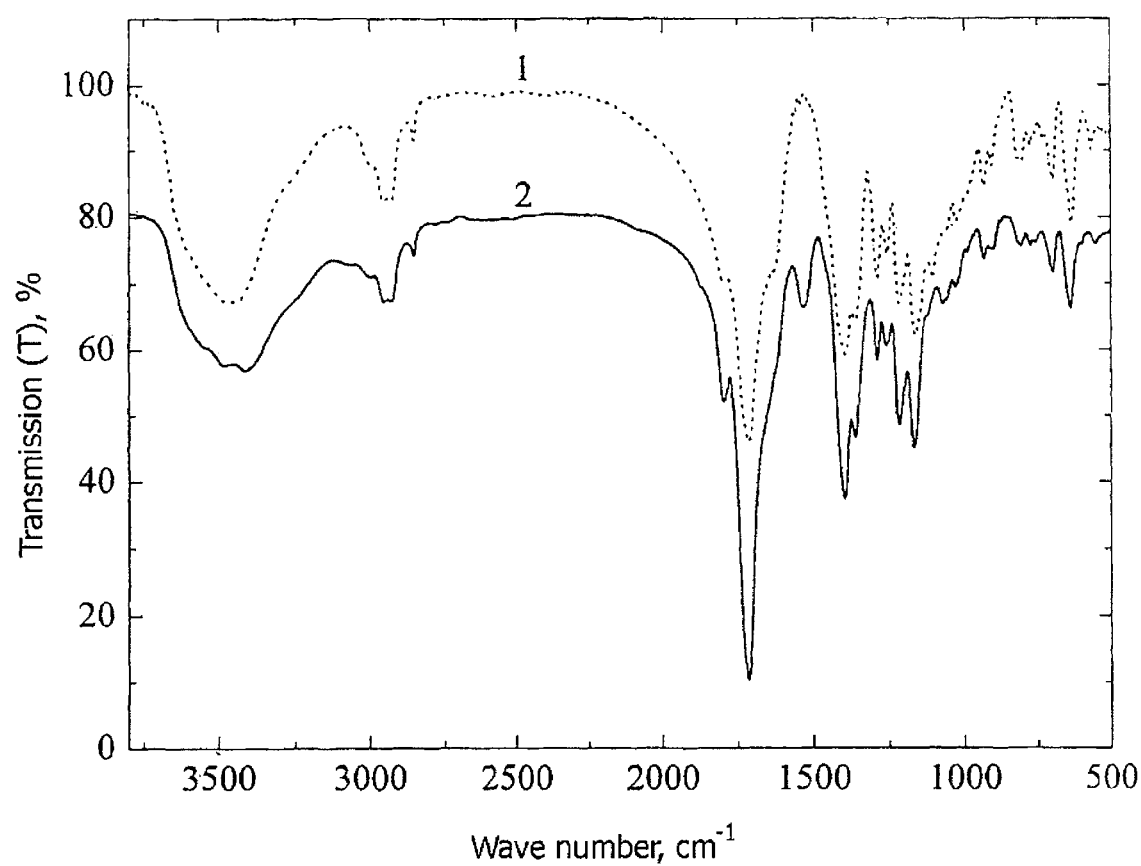
FIG. 5. The results of IR spectroscopy analysis: 1—Polysuccinimide (PSI) prepared by a conventional liquid-phase catalytic polymerization; 2—Nickel-copper alloy nanoparticles treated as described in Example of the preferred embodiments of the invention and isolated from the reaction mixture with the aid of hot water washing and magnetic separation.
Figure 6:
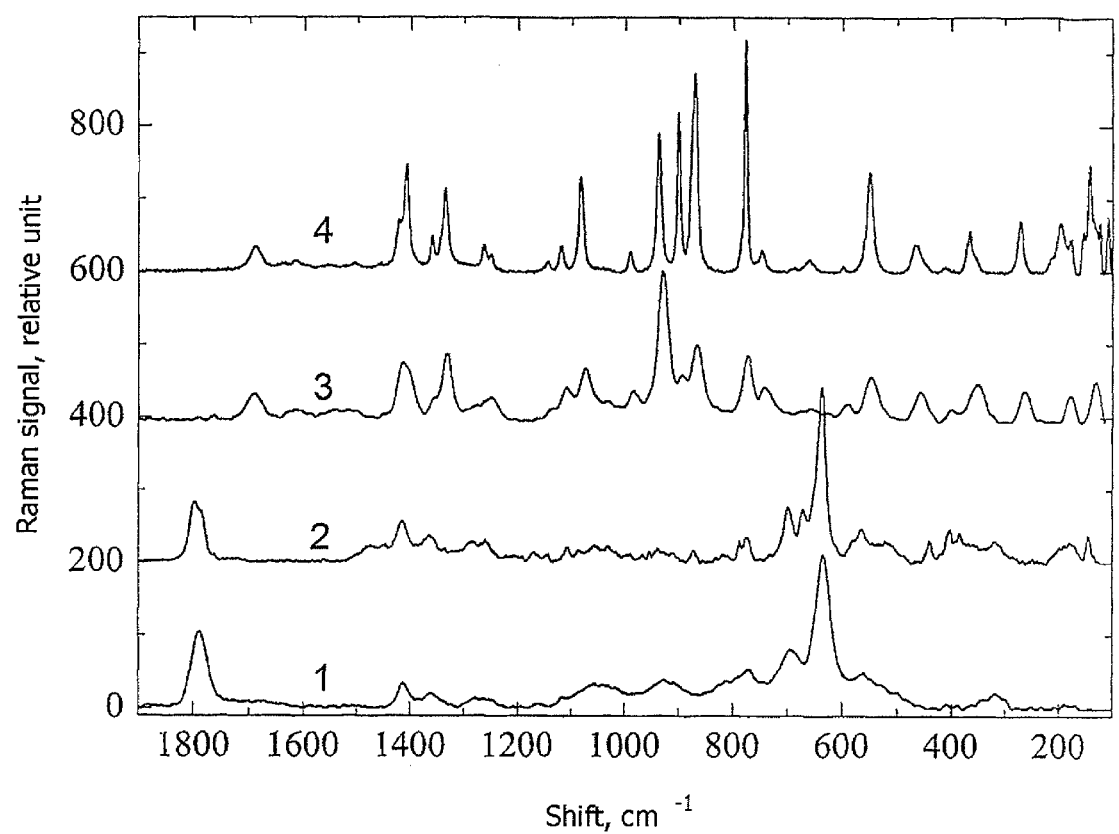
FIG. 6. The results of Raman analysis: 1—Raman spectrum of Nickel-copper alloy nanoparticles treated as described in the Example of the preferred embodiments of the invention and isolated from the reaction mixture with the aid of hot water washing and magnetic separation; 2—Raman spectrum of a standard PSI sample prepared by the conventional liquid-phase catalytic polymerization; 3—Raman spectrum of the water-soluble products formed upon realization of the claimed method embodiment; 4—Pristine crystalline aspartic acid.

The molecular structure of the organic coating on the nickel-copper alloy nanoparticles was confirmed by IR spectroscopy (FIG. 5) and Raman spectroscopy (FIG. 6). FIG. 5 shows that IR spectrum of PSI independently prepared by the conventional liquid-phase catalytic polymerization (curve 1) and that of the nickel-copper alloy nanoparticles which were treated as described in the example of the preferred embodiments of the invention and then isolated from the reaction mixture with the aid of hot water washing and magnetic separation (curve 2) are actually identical. Note, that metals (in particular nickel and copper) effectively reflect the electromagnetic infrared waves and give no absorption bands in IR spectra. So, the spectrum in FIG. 5 reveals only the organic coating material formed on metallic nanoparticles. Thus, IR spectroscopy also confirmes that the organic coating on the magnetic particles surface is represented by polysuccinimide.

FIG. 6 shows a series of Raman spectra representing: (1) Nickel-copper alloy nanoparticles treated as described in the example of the preferred embodiments of the invention and then isolated from the reaction mixture with the aid of hot water washing and magnetic separation; (2) PSI prepared by the conventional liquid-phase catalytic polymerization; (3) Water soluble products formed upon realization of the claimed method; (4) Pristine crystalline L-aspartic acid. Comparison of the spectra shows that the spectra 1 and 2 as well as 3 and 4 are quite similar within the indicated pairs. Such similarity of these spectra definitely proves that the coating on the particles to consists of polysuccinimide (spectra 1 and 2), whereas water washings contain only the unreacted aspartic acid (spectra 3 and 4).

Therefore, the claimed method is suitable to prepare the polymeric coating of PSI on the ferromagnetic nanoparticles by polymerization of aspartic acid as the result of thermal action caused by absorption of electromagnetic waves by the magnetic particles.

INDUSTRIAL APPLICABILITY

The claimed method for preparing the polymer coating on particles is applicable for creation of the systems of vector delivery of drugs and biologically active agents and usable in medical and veterinary practice, medical and pharmacological industry, biotechnology, agriculture, industries of cosmetic and hygienic means, biocompatible materials and in other fields. The elaborated method is applicable in promising technological developments for creation of new nanomaterials and highly dispersed systems with special properties.

The invention claimed is:

1. Method of producing a polymer coating on particles capable of absorbing microwaves, the particles having a surface, the method comprising:
   (a) forming a reaction system by mixing the particles with monomers in the absence of an inert solvent as a dispersing medium, and
   (b) irradiating the reaction system with microwave radiation capable of being absorbed by said particles to carry out a polymerization reaction to form the polymer coating on the particle surface; wherein amino acids are used as said monomers.

2. Method according to claim 1, wherein aspartic acid is used as amino acid.

3. Method according to claim 1, wherein inorganic magnetic particles are used as the particles.

* * * * *